US012661267B2

(12) United States Patent
Righi et al.

(10) Patent No.: US 12,661,267 B2
(45) Date of Patent: Jun. 23, 2026

(54) TYPE GH LIQUID CRYSTAL PROTECTIVE GLASSES AND COVERING STRUCTURAL FRAME

(71) Applicant: OUT OF S.R.L., Brescia (IT)

(72) Inventors: Federico Righi, Brescia (IT); Roberto Righi, Brescia (IT)

(73) Assignee: OUT OF S.R.L., Brescia (IT)

( * ) Notice: Subject to any disclaimer, the term of this patent is extended or adjusted under 35 U.S.C. 154(b) by 238 days.

(21) Appl. No.: 18/687,469

(22) PCT Filed: Sep. 20, 2022

(86) PCT No.: PCT/IB2022/058863
§ 371 (c)(1),
(2) Date: Feb. 28, 2024

(87) PCT Pub. No.: WO2023/047271
PCT Pub. Date: Mar. 30, 2023

(65) Prior Publication Data
US 2024/0366430 A1 Nov. 7, 2024

(30) Foreign Application Priority Data
Sep. 21, 2021 (IT) ......................... 102021000024203

(51) Int. Cl.
*A61F 9/02* (2006.01)
(52) U.S. Cl.
CPC .................................... *A61F 9/023* (2013.01)
(58) Field of Classification Search
CPC ................................ A61F 9/023; G02C 7/101
See application file for complete search history.

(56) References Cited

U.S. PATENT DOCUMENTS 5,841,507 A 11/1998 Barnes
11,213,429 B1 * 1/2022 Li ......................... G02F 1/1337

FOREIGN PATENT DOCUMENTS

CN 105759456 A 7/2016
JP 2001183616 A 7/2001
WO 8911673 A1 11/1989

OTHER PUBLICATIONS

International Search Report for International Patent Application No. PCT/IB2022/058863, mailed Nov. 25, 2022.

* cited by examiner

*Primary Examiner* — James C. Jones
(74) *Attorney, Agent, or Firm* — CANTOR COLBURN LLP

(57) ABSTRACT

Provided are protective glasses and/or sunglasses equipped with a frame adapted to support a lens assembly having at least one structural lens made of plastics material and at least one liquid crystal (LC) film of the guest host type arranged on an inner side of the at least one structural lens and controlled by an electronic board powered by an energy source. The at least one structural lens has a free edge extending beyond an outline of the at least one LC film at which the lens assembly is fixed to the frame. A free space is provided between the frame and the at least one LC film. The frame is provided with a vertically projecting rib covering the free edge and the free space. The rib not only reduces deformations of the lens assembly, but also prevents infiltrations of light around the LC film that would compromise comfortable vision.

14 Claims, 6 Drawing Sheets

6

91

9

10

8

3

2

9

8

9

8

111

21

11

2

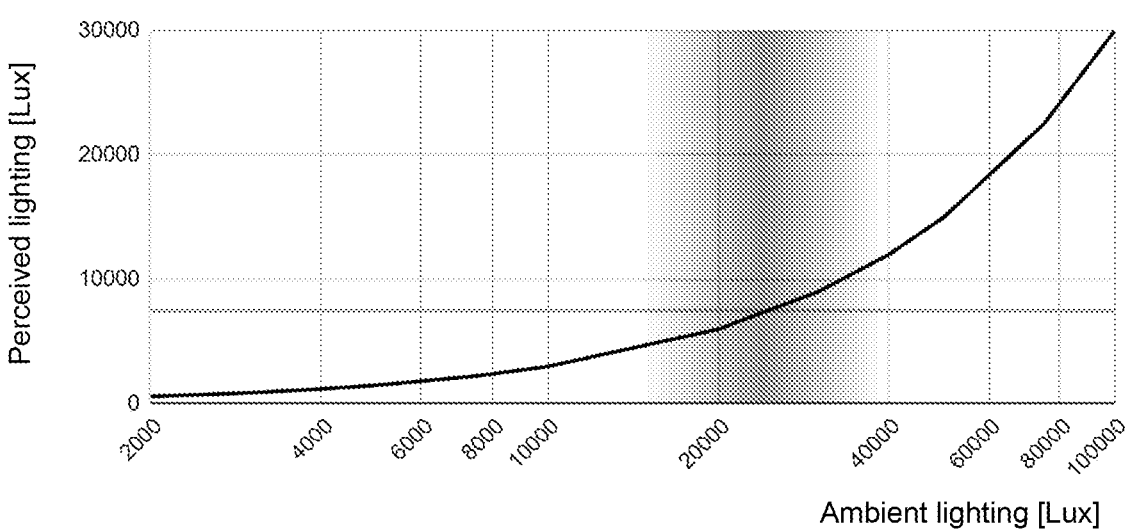
FIG.6 - PRIOR ART
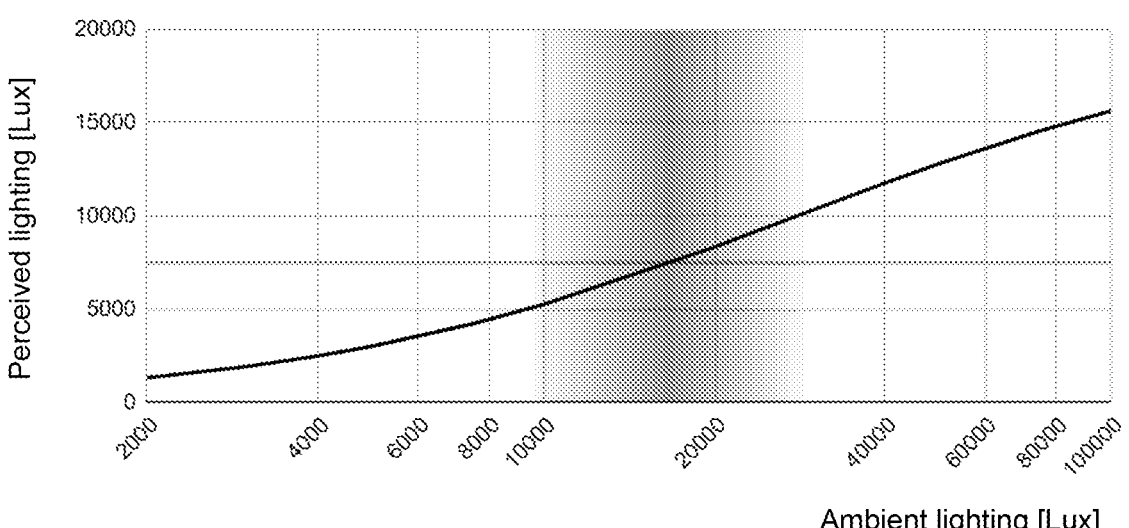
FIG.7 - PRIOR ART

TYPE GH LIQUID CRYSTAL PROTECTIVE GLASSES AND COVERING STRUCTURAL FRAME

CROSS-REFERENCE TO RELATED APPLICATIONS

This application is a National Phase Application of PCT International Application PCT/IB2022/058863, having an International Filing Date of Sep. 20, 2022 which claims priority to Italian Application No. 102021000024203 filed Sep. 21, 2021, each of which is hereby incorporated by reference in its entirety.

FIELD OF THE INVENTION

The object of the present invention is protective glasses for the practice of sports activities or for the use of transport means.

BACKGROUND OF THE INVENTION

In many cases during the practice of sports, it is necessary to use glasses to protect the eyes from wind, particles, excessive light, etc.

The same requirement is found when using open means of transport such as traditional and electric bicycles, scooters or skateboards.

Those glasses that are currently on the market are very capable of protecting the eyes of the user from wind and particles.

As regards protection from light, there are many types of filters that reduce the amount of light that reaches the eye of the user, and each of these filters is suitable for specific light conditions. Current European legislation, for example, divides optical filters into five categories and describes, for each thereof, under which conditions these filters are suitable for protecting the eye of the user while allowing for optimal vision.

In sport and when using transport means, however, ambient light conditions may change considerably and very quickly: it is sufficient to consider, for example, entering a road tunnel. Therefore, for this type of activity, not only is the use of a single lens not optimal, but it is also not possible to change the type of lens in response to any change in ambient brightness conditions.

In response to this problem, photochromic lenses have been developed that use chemical reactions to provoke a decrease in lens transparency as a result of exposure to light radiation. Photochromic lenses are however rather slow particular in in increasing transmission, and therefore require a few minutes for a complete transition.

In addition, the use of chemical reactions to decrease the transparency of the filter results in poor control of the lens activation curve, and therefore of the filter transmission as a function of the amount of incident light. For example, this type of lens often darkens partially in situations where the lighting level is less than optimal, even going so far as to make the situation worse. This second aspect is aggravated by the high sensitivity of these filters to ultraviolet light. In fact, ultraviolet light is often present in good quantities even in conditions where there is poor lighting, which may result in a photochromic lens being rather dark even under conditions of poor lighting.

As if this were not enough, all of these aspects are further aggravated in the presence of low temperatures, which always tend to result in photochromic lenses being partially obscured.

Electrochromic lenses are also known that typically use polymers that may change optical properties when a magnetic field is applied. Said lenses, while faster than photochromic lenses, are still quite slow. Moreover, the high power required to achieve the change in state limits the maximum number of possible changes, making this type of lens functional for automatic adaptation to ambient light only in the presence of bulky batteries.

Finally, lenses that use layers of liquid crystals are known and are the only ones that are able to react quickly to changes in ambient light. However, lenses of this type are still substantially unused in commonly used products, given the persistence of a number of issues, including: low maximum brightness of the filter, the presence of unwanted polarizations, interference with other transparent elements, and undesirable reactions to mechanical stresses. For these reasons, said lenses find real application in the field of protective devices for welding, in which TN (twisted nematic) planar liquid crystal LC screens are widely used. However, said screens are not suitable for sunlight protection under normal conditions, as they are in fact too dark in their maximum transmission state and have a very small field of vision.

Device application techniques using GH (guest-host) liquid crystals are also known. This type of liquid crystal does not use polarizing filters and may therefore achieve transparencies that are greater than 50%, making it potentially more suitable for use in sunlight protective devices under normal conditions. However, even this type of lens presents a series of problems, due to which devices made in this way are not currently on the market. The following are some of the issues associated with this technology.

1) GH liquid crystal layers are affected by mechanical stresses that result in strong alterations in the local transparency level of the LC film. Sunglasses, because of how they are constructed, involve mechanical stresses on the lens that are too great to be able to use an LC film of the GH type.

2) To reduce the mechanical stresses mentioned above, a possible solution would be to apply an LC film to a structural lens so that the LC film is relatively independent of the deformations of the lens. However, this configuration results in annoying light infiltration from the outer perimeter of the LC film and therefore a reduction in optical quality.

3) The most common lenses for making protective glasses are obtained by means of injection molding. This technique has considerable advantages, but when applied to glasses lenses it leads to the formation of internal tensions within the lens which, in combination with a GH LC film, create an annoying "rainbow" effect. A possible solution to this problem would be to use thermoformed lenses. However, this type of lens has a much lower optical quality and precision. Moreover, with this technique it is not possible to create optically "correct" lenses.

4) All dynamic lenses marketed to date lack adequate control of the activation curve, or of the function between the ambient lighting level and the reduction in the transmission of visible light. In the absence of accurate control of such an activation curve, it is substantially impossible to obtain a device that is truly effective in maintaining an optimal lighting level as perceived by the user over a wide range of ambient lighting levels. This issue has not yet been resolved.

SUMMARY OF THE INVENTION

The object of the present invention is that of obtaining glasses that are actually capable of offering optimal protection from light not only under the most common lighting conditions but also following sudden changes in such conditions, while always ensuring comfortable and effective vision.

This purpose is achieved by protective glasses and/or sunglasses, a lens assembly and a method for controlling the level of transparency of a lens assembly as described and claimed herein. Advantageous embodiments of the present invention are also described.

BRIEF DESCRIPTION OF THE FIGURES

The features and advantages of the glasses according to this invention will become apparent from the following description, given as a non-limiting example in accordance with the accompanying drawings, wherein:

FIG. 6 shows the relationship between ambient lighting and perceived lighting for a traditional static lens with 30% VLT (visible light transmission);

FIG. 7 shows the relationship between ambient lighting and perceived lighting using a photochromic lens;

DETAILED DESCRIPTION

Figures 1, 2:
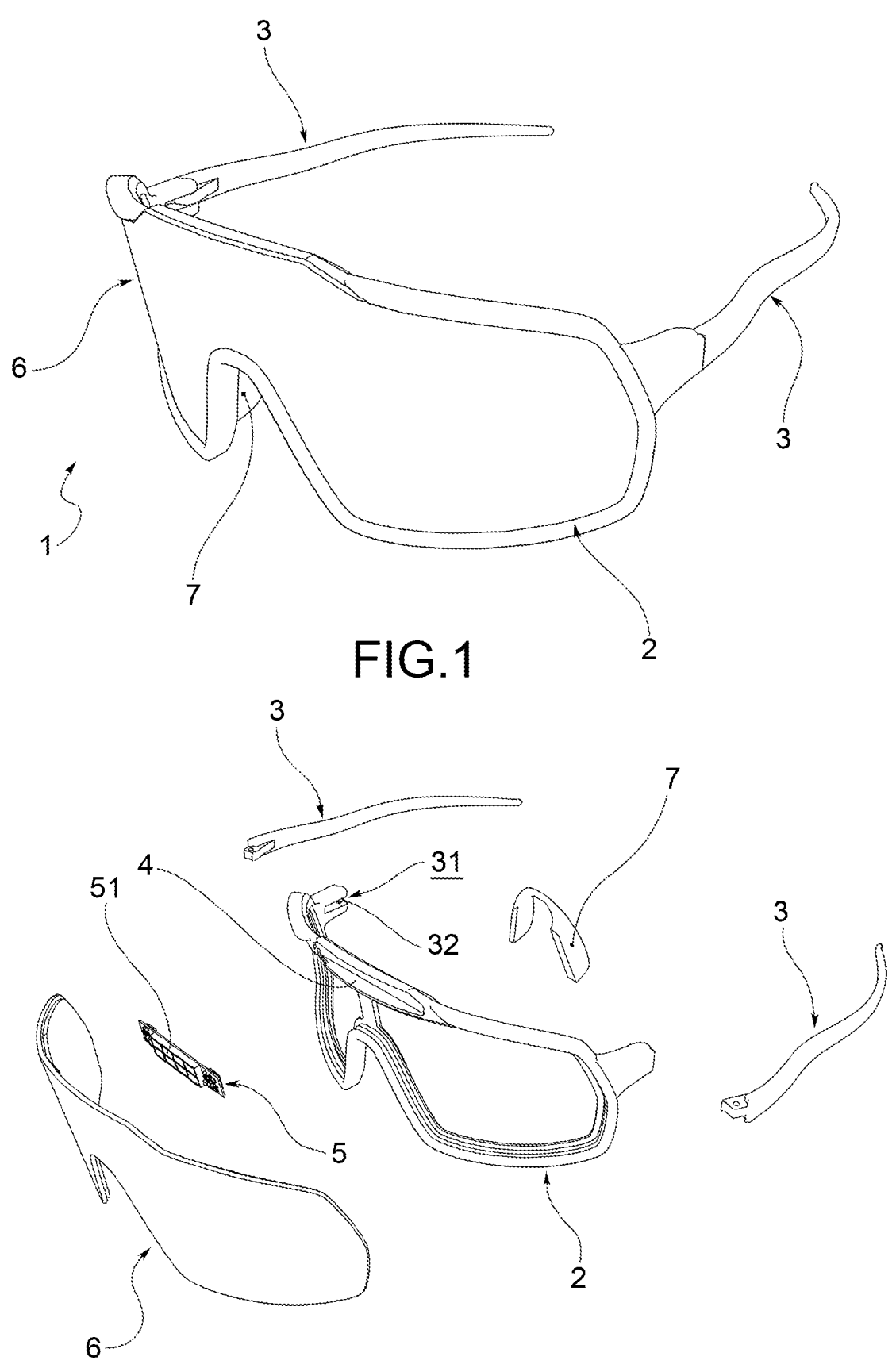
FIG. 1 shows a prospective view of protective glasses according to the present invention in one embodiment.
FIG. 2 shows an exploded view of the protective glasses shown in FIG. 1.

With reference to the appended figures, 1 has been used to collectively denote protective glasses for the practice of sports activities or for the use of motorized vehicles according to the present invention. In particular, the protective glasses 1 are also sunglasses.

The glasses 1 comprise a frame 2 adapted to support a lens assembly 6. As may be seen in FIG. 1, the frame 2 completely follows the perimeter of the lens assembly 6.

As shown in FIG. 6, the lens assembly 6 comprises a structural lens 8 and at least one liquid crystal film 9 (hereinafter LC film) controlled by an electronic board 5.

Preferably, the frame 2 is made of a polymer matrix composite material, for example Nylon, polycarbonate, epoxy resin or polyester. Preferably, the frame 2 is made of a polymer matrix composite material and with reinforcing materials, such as for example glass or carbon fiber, glass microspheres, or graphene.

In an alternative embodiment, the frame 2 is made of lightweight metal material such as aluminum alloy, titanium, or magnesium.

Depending upon the material chosen, the frame 2 is obtained by means of injection molding, or possibly by forging, die-casting or sheet metal molding.

Advantageously, the materials listed above make it possible for the frame 2 to be sufficiently rigid in order to avoid deformations of the lens assembly 6 during use, which deformations would be transmitted to the LC film 9 thereby compromising the optical uniformity thereof.

Preferably, the glasses 1 comprise a pair of temples 3 which are hinged to the frame and are able to fold back on top of one another in order to reduce the size of the glasses when not in use.

Preferably, the assembly of the temples 3 to the frame does not require the use of through pins. In fact, each temple 3 is assembled to the frame by means of interlocking with a temple seat 31 of the frame 2, which seat is defined between a pair of protrusions or concavities 32, which are semi-spherical and facing one another, so that a forced rotation of the temple 3 beyond the end of travel does not result in breakage, but simply disassembly from the frame 2.

As may be seen in FIG. 2, the temples 3 have an ergonomic shape, characterized by a substantially S-shaped, i.e. corrugated, curvature which, at the end part of the temple, follows the curvature of the head of the user but, at the part near the hinging point, moves away from the head of the user so as to be assembled to the frame. Advantageously, this wavy shape increases the contact surface with the head of the user, thus improving comfort and retention; it also makes it possible and comfortable to use the glasses beneath helmets, headgear, caps and bands, etc.

Preferably, the temples 3 are made of a material having an elastic modulus less than or equal to half the elastic modulus of the material chosen for the frame 2. Advantageously, this configuration causes the deformations of the glasses 1 necessary for positioning on the face of the user to act mainly on the temples 3, thereby avoiding excessive deformations of the frame 2. In this way, the deformations and stresses acting upon the structural lens 8 and, ultimately, those acting upon the LC film 9 are also contained.

Preferably, the frame 2 is equipped with a rubber nose piece 7 which is interlockingly assembled and which facilitates the retention of the glasses 1 on the nose of the user.

The frame 2 is provided with a seat or recess 4 in which at least one energy source is housed, for example a photovoltaic cell 51, or an entire electronic board 5 that includes a photovoltaic cell 51.

Advantageously, said recess 4 is positioned in the front, upper, central part of the frame 2, as seen in FIG. 2, so as not to interfere with the visual field of the user.

In one embodiment, the recess 4 houses only the energy source, for example a photovoltaic cell 51, while the electronic board 5 is positioned in another seat provided, for example, on the sides of the frame 2, or inside the temples 3, or in another optimal position for the specific application.

Preferably, the photovoltaic cell 51 acts, at the same time, both as a sensor and as an energy source for the operation of the LC film 9. Advantageously, this configuration makes it possible to avoid the use of batteries, thus reducing costs and increasing the reliability of the glasses 1.

In one embodiment, the photovoltaic cell 51 is flexible and/or follows the curvature of the structural lens 8.

The electronic board 5 is waterproof, which means that it is protected by a coating, potting or other forms of waterproof protective treatment.

As mentioned above, the frame 2 surrounds the lens assembly 6 comprising the structural lens which is preferably made of a plastics material, for example polycarbonate.

Preferably, the structural lens 8 protects the electronic board 5 at the front, which board is protected at the rear by the walls of the recess 4 located in the frame 2. Advantageously, this configuration provides mechanical and chemical protection to the electronic board 5. It also filters the light reaching the photovoltaic cell 51 in the same way that the light reaching the eye of the user is filtered, excluding the absorption of the structural lens 8. In this way, the input signal of the electronic board 5 will be correctly calibrated with respect to the perception of the user. For example, the input signal of the electronic board 5 will not be affected by ultraviolet radiation, as indeed it should be, because the ultraviolet radiation is already stopped by the structural lens 8.

The structural lens 8 is preferably produced by means of injection molding; in other exemplary embodiments, the structural lens is produced by thermoforming, stereolithography or another additive manufacturing technique.

In one exemplary embodiment, the structural lens 8 has mirroring, anti-reflective, anti-scratch, hydrophobic or oleophobic treatments or other treatments that are suitable for the specific application.

In one exemplary embodiment, the structural lens 8 has multilayer, even opaque, mirroring treatments. In a variant of such an example, the characteristics of the mirroring treatments differ within different areas of the structural lens 8.

In the lens assembly 6, the LC film 9 is arranged internally with respect to the structural lens 8. Preferably, the LC film 9 is laminated, preferably by means of optical glue, on the inner face of the structural lens 8.

Preferably, the LC film 9 is a GH liquid crystal film. In this type of LC film, dichroic pigments are dispersed within a matrix of liquid crystals, and the magnetic field directs the orientation of the liquid crystals which, in turn, direct the orientation of the pigments. Typically in the "active" state, the crystals assume a helical configuration and the pigments are arranged in planes parallel to the surface of the film, while in the "inactive" state, crystals and pigments are arranged perpendicularly to the surface of the film.

Preferably, the LC film 9 has a visible light transparency (VLT) of at least 60% in the most transparent state thereof and of at most 25% in the most opaque state thereof. For example, the LC film may have a VLT of about 15% in the most opaque state thereof and a VLT of about 65% in the most transparent state thereof. Preferably, as may be seen in FIGS. 4 and 5, the outline of the LC film 9 is contained within the outline of the structural lens 8. The portion of the outline of the structural lens 8 that is not occupied by the outline of the LC film 9 defines a free edge 11 at which the structural lens 8 is attached to the frame 2. Furthermore, the frame 2 is not in direct contact with the LC film 9, as there is a space or gap 111 provided.

Figures 3, 4, 5:
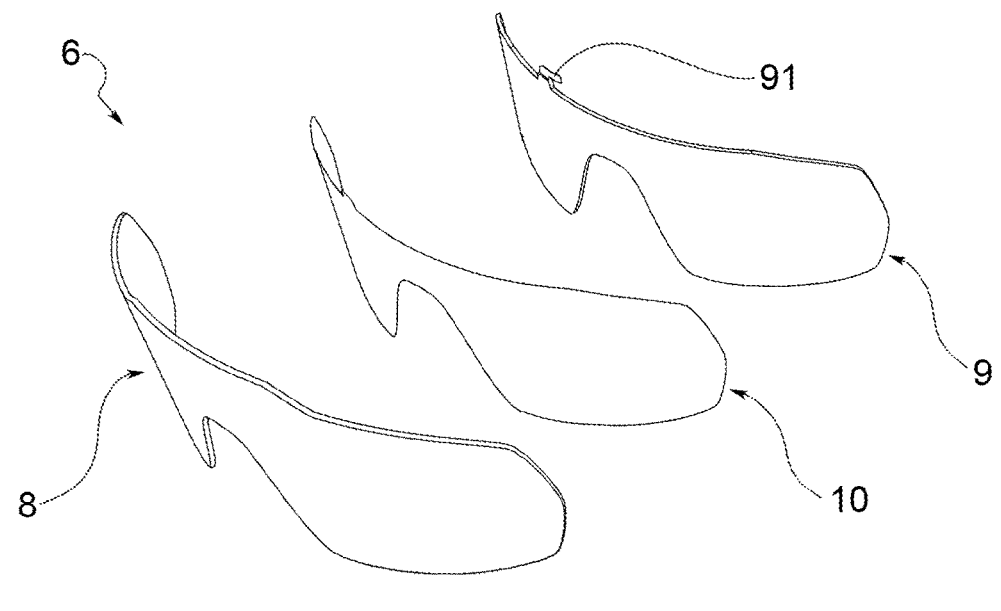
FIG. 3 shows an exploded view of the lens assembly of the protective glasses of FIG. 1.
FIG. 4 shows a cross-sectional view of the protective glasses of FIG. 1.
FIG. 5 shows a detail of FIG. 4.

Preferably, the frame 2 has a substantially L-shaped cross section, as seen in FIG. 5, which means that the frame 2 is internally provided with a vertical rib 21 covering the free edge 11 and the gap 111. Advantageously, this configuration prevents infiltrations of light around the LC film 9 that would compromise comfortable vision. Furthermore, the rib 21 of the frame makes it possible to reduce deformations of the lens assembly 6.

The LC film 9 is controlled by the electronic board 5 to which it is preferably connected by means of a flexible printed circuit board (FPC) 91.

The protective glasses 1 are equipped with an electronic board 5 that controls the activation of the LC film 9 as a function of the ambient lighting level according to a non-linear activation curve. The activation curve determines that the LC film 9 should remain substantially in the state of maximum transparency thereof until reaching a certain lighting threshold 131, after which the LC film 9 begins to reduce the transparency as the ambient lighting increases.

As seen in FIG. 3, preferably between the structural lens 8 and the LC film 9, a depolarizing layer 10 is laminated. The depolarizing effect of the depolarizing layer 10 is preferably obtained by means of a birefringent film characterized by a wave phase shift between the two optical axes of greater than 1500 nm.

Figure 9:
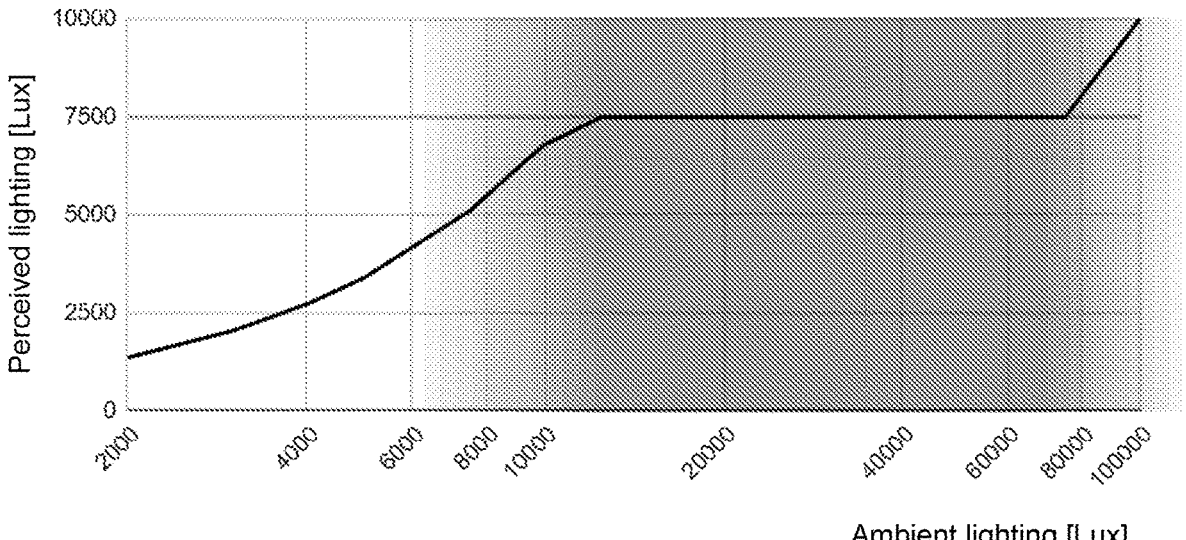
FIG. 9 shows the relationship between ambient lighting and perceived lighting in an exemplary embodiment of the present invention.

FIGS. 6, 7 and 9 show a graph depicting the relationship between ambient lighting (in Lux) and perceived lighting (in Lux) depending upon the lens used for the glasses. The graph also shows:
  a horizontal line indicating the optimum lighting level for the practice of sports activities (7500 Lux);
  a gray area indicating the optimum usage range of the lens under analysis.

FIG. 6 shows the relationship between ambient lighting and perceived lighting when using a traditional lens with 30% VLT (visible light transmission). It should be noted that in this case the lens is suitable for a specific light condition (the very small gray area of the graph) and therefore has a limited optimal usage range.

FIG. 7 shows the relationship between ambient lighting and perceived lighting when using a typical photochromic lens. Although the objective of a photochromic lens is to have the right transparency in every situation, in reality the activation curve of the pigments is poorly controllable. For example, the transparency of the filter typically begins to decrease considerably long before it has reached the optimal lighting level. In fact, photochromic lenses also have a limited optimal usage range (highlighted by the gray area in the graph) as with traditional lenses.

Figure 8:
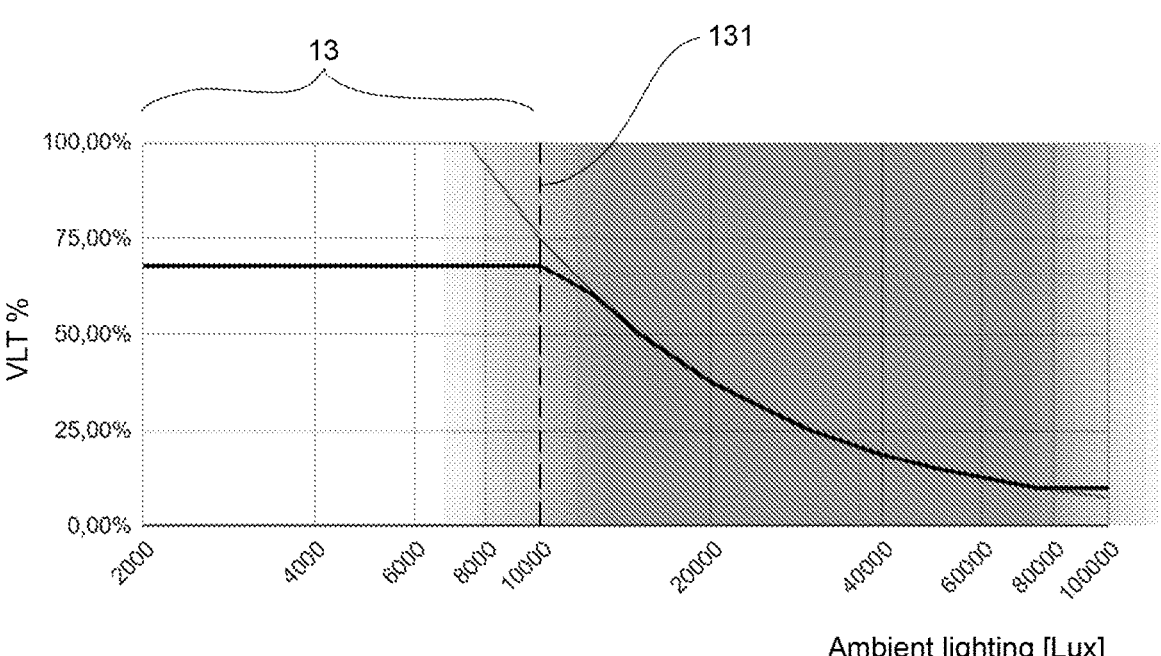
FIG. 8 shows the relationship between ambient lighting and VLT (visible light transmission) of the lens in an exemplary embodiment of the present invention.

FIG. 8 represents the relationship between ambient lighting and the visible light transmission level (VLT=visible light transmission) of a lens assembly 6 according to the present invention, wherein the electronic board 5 controls the LC film 9 and keeps it in the deactivated state thereof (maximum visible light transmission level) within a low lighting range, indicated by the reference number 13 in FIG. 8.

The amplitude of the range 13 is defined at the top by a threshold level, indicated by the reference number 131 in FIG. 8.

In one exemplary embodiment, the threshold level 131 is fixed and calculated by dividing an optimal perceived lighting level, set at 7500 Lux for the practice of sports activities or the use of transport means, by the maximum visible light transmission level, i.e. the maximum level of transparency, of the lens assembly 6, with a tolerance of 25%.

The threshold level 131 corresponds to the ambient lighting level below which the lighting level perceived by the user through the lens assembly 6 at the maximum visible light transmission level thereof is lower than the optimal level and consequently it is appropriate that the LC film 9 remains totally deactivated and therefore in the state of maximum transparency thereof.

When the ambient lighting level is above the threshold level 131, the electronic board 5 controls the visible light transmission level and therefore the transparency of the LC film 9 by decreasing it as the ambient lighting level increases, according to a particular control function, until the minimum transparency level of the LC film 9 is reached, i.e. the minimum visible light transmission level.

Within the low-light range 13, the value of the visible light transmission VLT level of the LC film 9 is determined by the control function which is defined as follows:

$$VLT = 7500\,Lux/(t \cdot la)$$

where "t" is the visible light transmission level of the structural lens 8 and "la" is the ambient lighting level expressed in Lux.

The graph in FIG. 9 shows the relationship between ambient lighting and the lighting perceived by a user wearing protective glasses 1 in accordance with this invention. As may be seen from the large gray area on the graph, the protective glasses 1 provide optimal perceived lighting over a wide range of ambient brightness. The protective glasses 1 according to the present invention are therefore not suitable for a specific lighting situation, but allow for optimal vision over a fairly wide lighting range.

In a further exemplary embodiment, the threshold level 131 is variable according to the average ambient lighting level with reference to a particular time interval, for example between 30 seconds and 5 minutes. Advantageously, the protective glasses 1, in taking advantage of the ability of the human eye to slowly adapt to changes in ambient light, make it possible to eliminate changes in perceived lighting due to sudden changes in the ambient lighting level.

Figure 10:
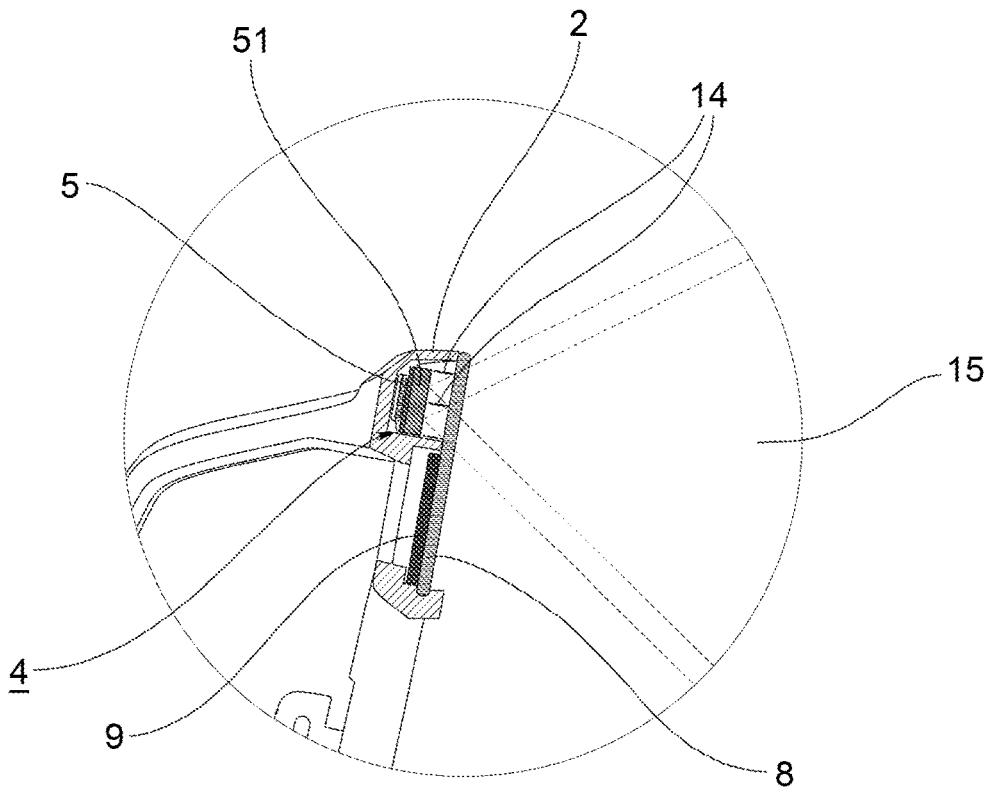
FIG. 10 shows a detail of the longitudinal section of protective glasses according to the present invention, in a further embodiment.
Figure 11:
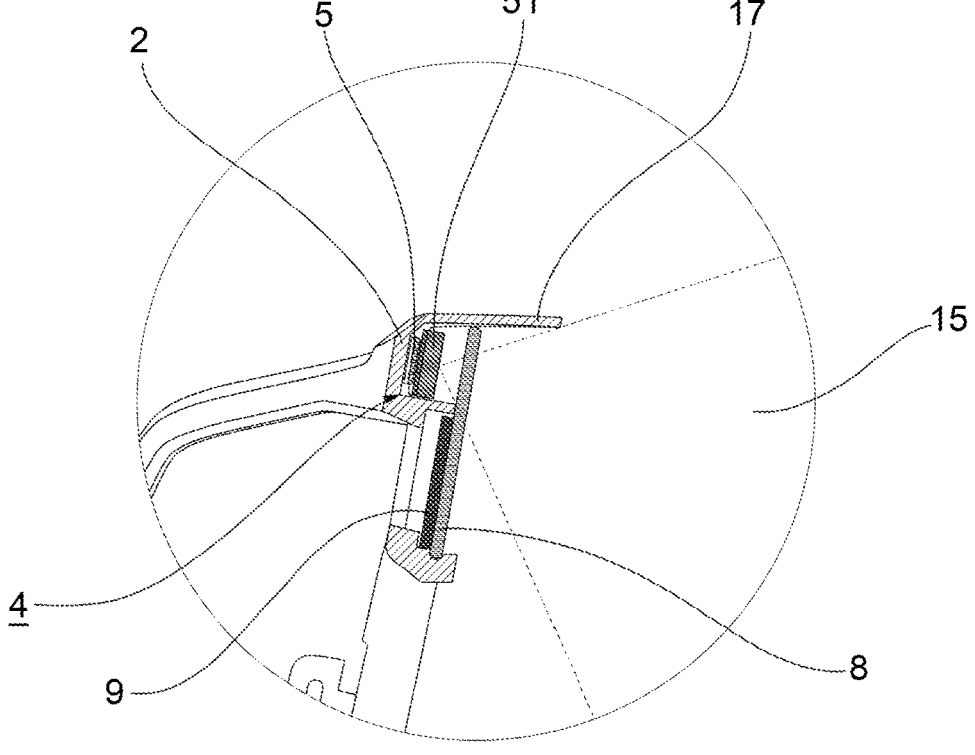
FIG. 11 shows a detail of the longitudinal section of protective glasses according to the present invention, in yet a further embodiment.
Figure 12:
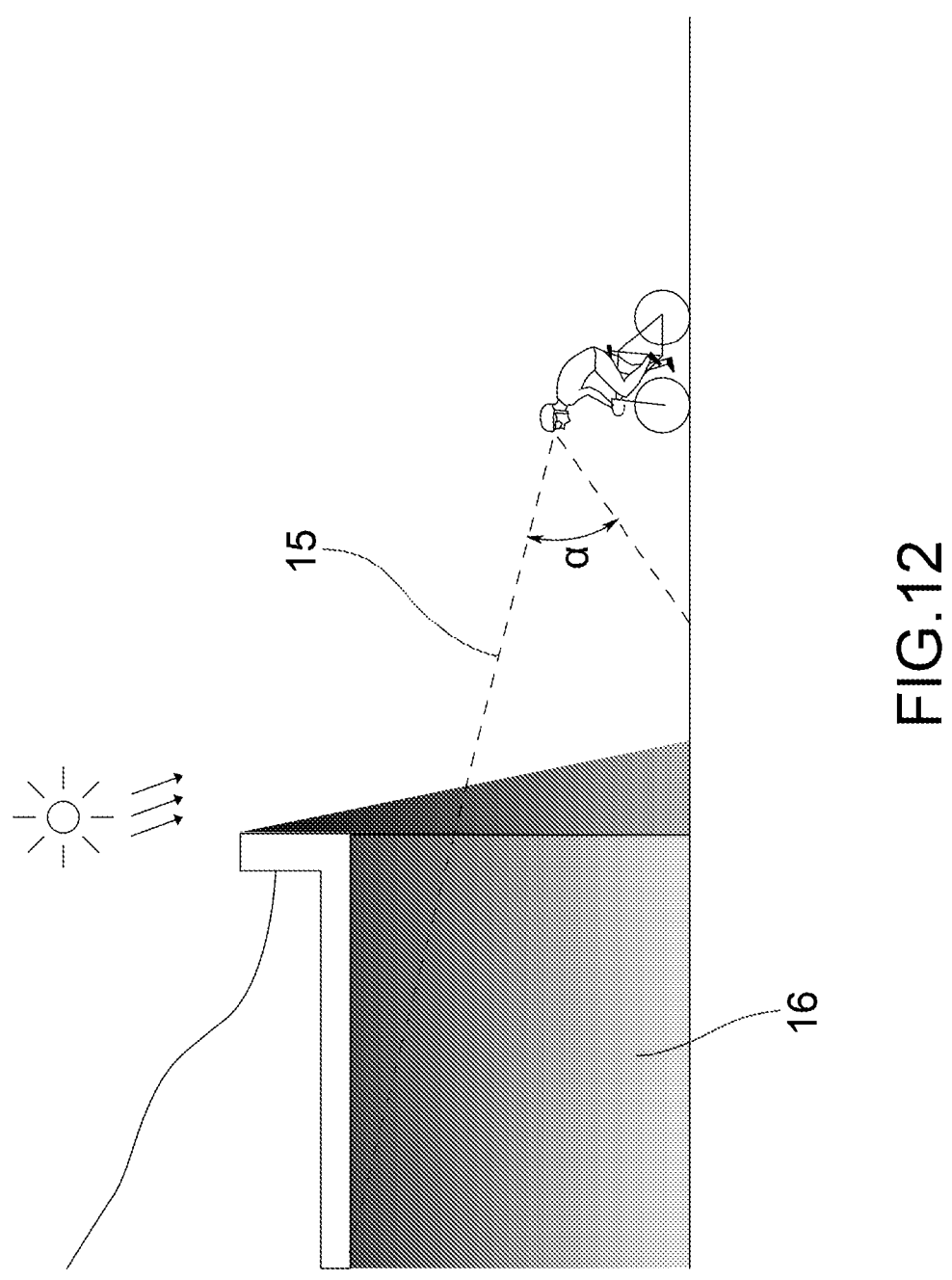
FIG. 12 shows, in a schematic manner, the operation of a sensitivity cone applied to the glasses according to the present invention during use.

In a further exemplary embodiment, shown in FIGS. 10 to 12, the circuit board 5 receives, as input, the ambient lighting level of a predefined area of the field of view of the user, for example of a sensitivity cone 15. Preferably, the sensitivity cone 15 has an opening angle α of between 90 degrees and 10 degrees, and is oriented towards the front/lower part of the user, as shown in FIG. 12.

The protective glasses 1 are equipped with a device for controlling the opening angle α of the sensitivity cone 15.

In the example of FIG. 10, the device for controlling the opening of the sensitivity cone 15 is defined by means of slats 14 arranged inside the recess 4, in front of the photovoltaic cell 51.

In the example in FIG. 11, the device for controlling the opening of the sensitivity cone 15 is defined by means of a visor 17 protruding from the frame 2 frontally and above the recess 4 in which the photovoltaic cell 51 is contained.

In further embodiments, the opening of the sensitivity cone 15 is defined by means of lenses or mirrors in order to obtain similar results.

In an alternative exemplary embodiment, the protective glasses 1 comprise a sensor which is arranged inside the recess 4, next to the photovoltaic cell 51. In this way, by means of appropriate adaptation of the electronic board 5, it is possible to obtain the definition of the opening of the sensitivity cone even in the absence of a cumbersome physical device such as the slats 14 or the visor 17. In this example, the electronic board 5 uses the photovoltaic cell 51 as the only source of energy, while the sensor determines the ambient lighting value to be compensated for.

Advantageously, by virtue of the detection of the sensitivity cone 15, the lens assembly 6 is sensitive to part of the ground and to those objects that the user will shortly encounter along the way. Protective glasses 1 are thus obtained in which, with most common usage situations, the corrections thereof are substantially predictive.

FIG. 12 shows the case in which the protective glasses 1 are used by a cyclist who is preparing to traverse a tunnel. In this situation, the sensitivity cone 15 is occupied mostly by a poorly lit area (denoted by the number 16). In this situation, the input signal of the electronic board 5 will be reduced and the lens assembly 6, or rather the LC film 9, will assume the state of greater transparency thereof, notwithstanding that the cyclist is still lit by the sun. Advantageously, therefore, the cyclist is able to optimally see the ground within the poorly lit zone 16, even if there is a sudden change to the light, and even before reaching said zone, so as to be able to avoid or react to any obstacles or dangers such as potholes, stationary cars, boulders, etc.

In one embodiment of the present invention, the opening angle α of the sensitivity cone 15 is fixed, and is related to the typical speed of the specific activity for which the protective glasses 1 are designed. In fact, it is preferable to have a sensitivity cone with an opening that is smaller the higher the typical rate of movement of the user. Advantageously, this configuration allows the user to focus attention on those objects that will be reached at a time comparable to that of the reaction time.

In a further embodiment of the present invention, the opening angle α of the sensitivity cone 15 is variable, and is constantly adapted during use according to the input signal received from a speed sensor, for example a GPS sensor, an accelerometer system, or a system based upon optical sensors, for example based upon speckles.

In a further embodiment of the present invention, the device that determines the opening of the sensitivity cone 15, for example the slats 14, may be replaced by the user in order to be able to adapt the protective glasses 1 to more specific uses.

It is understood that a person skilled in the art, in order to meet contingent needs, could make modifications to the device described above, all of which are contained within the scope of protection as defined by the following claims.

The invention claimed is:

1. Protective glasses and/or sunglasses, comprising:

a frame adapted to support a lens assembly;

a lens assembly, at least partially surrounded by the frame and comprising:

at least one structural lens made of plastic material; and at least one liquid crystal film of the guest-host type, arranged on an inner side of the at least one structural lens and controlled by an electronic board powered by an energy source;

wherein:

the at least one structural lens comprises a free edge, extending beyond an outline of the at least one LC film, at which the lens assembly is fixed to the frame;

between the frame and the at least one LC film there is a free space; and the frame is provided with a vertically projecting rib covering said free edge of the at least one structural lens and said free space with the at least one LC film.

2. The protective glasses and/or sunglasses of claim 1, wherein the electronic board controls activation of the at least one LC film, provided with a maximum transparency state, as a function of an ambient lighting level so that the at least one LC film remains in said maximum transparency state until reaching a lighting threshold, after which the at least one LC film begins to reduce transparency as ambient lighting increases.

3. The protective glasses and/or sunglasses of claim 2, wherein said lighting threshold is calculated by dividing an optimal level of perceived lighting, established at 7500Lux, by a maximum visible light transmission level of the lens assembly, with a tolerance of 25%.

4. The protective glasses and/or sunglasses of claim 2, wherein said lighting threshold is variable in relation to an average ambient lighting measured in a time interval between 30 seconds and 5 minutes.

5. The protective glasses and/or sunglasses of claim 2, wherein said electronic board mainly reacts to the ambient lighting measured within a sensitivity cone oriented towards a front and/or lower part of a user's field of vision, and wherein the sensitivity cone has an opening angle ($\alpha$) between 90 and 10 degrees.

6. The protective glasses and/or sunglasses of claim 1, wherein the at least one LC film has a maximum VLT level less than 25% in a minimum transparency state thereof, and over 60% in a maximum transparency state thereof.

7. The protective glasses and/or sunglasses of claim 5, wherein the energy source of the electronic board is a photovoltaic cell, and wherein a control device of the opening angle of the sensitivity cone is present in the form of:

a lamellar structure arranged in front of said photovoltaic cell; or a visor, protruding from the frame, frontally and above said photovoltaic cell.

8. The protective glasses and/or sunglasses of claim 1, further comprising a pair of temples hinged to the frame, said pair of temples being made of a material having an elastic modulus lower than half of a material of which the frame is made.

9. The protective glasses and/or sunglasses of claim 1, wherein said energy source consists of one or more photovoltaic cells.

10. A protective and/or sun lens assembly, comprising:

at least one structural lens made of plastic material; and at least one liquid crystal film of the guest-host type, arranged on an inner side of the at least one structural lens and controlled by an electronic board powered by an energy source;

wherein the electronic board controls activation of the at least one LC film, provided with a maximum transparency state, as a function of an ambient lighting level so that the at least one LC film remains in said maximum transparency state until reaching a lighting threshold, after which the at least one LC film begins to reduce transparency as ambient lighting increases.

11. A method for controlling a level of transparency of a protective and/or sun lens assembly, said protective and/or sun lens assembly comprising at least one structural lens made of plastic material and at least one liquid crystal film of the guest-host type, arranged on an inner side of the at least one structural lens and controlled by an electronic board powered by a photovoltaic cell, said method comprising:

controlling activation of the at least one LC film, provided with a state of maximum visible light transmission level, by the electronic board as a function of an ambient lighting level as follows:

maintaining the at least one LC film in the state of maximum VLT level until a lighting threshold is reached; and once the lighting threshold has been exceeded, reducing the maximum VLT level as ambient lighting increases.

12. The method of claim 11, wherein:

said lighting threshold is fixed and calculated by dividing an optimal level of perceived lighting, established at 7500Lux, by the maximum VLT level of the protective and/or sun lens assembly, with a tolerance of 25%; or said lighting threshold is variable in relation to an average ambient lighting measured in a time interval between 30 seconds and 5 minutes.

13. The protective glasses and/or sunglasses of claim 1, wherein the energy source is positioned behind the at least one structural lens and outside a perimeter of the at least one LC film.

14. The protective glasses and/or sunglasses of claim 1, wherein the energy source is positioned outside a perimeter of the at least one LC film in an upper central part of the protective glasses and/or sunglasses.

* * * * *